United States Patent [19]

Esch

[11] Patent Number: 5,701,905
[45] Date of Patent: Dec. 30, 1997

[54] GUIDE CATHETER WITH SENSING ELEMENT

[75] Inventor: Brady Esch, Sunnyvale, Calif.

[73] Assignee: Localmed, Inc., Palo Alto, Calif.

[21] Appl. No.: 557,753

[22] Filed: Nov. 13, 1995

[51] Int. Cl.[6] ............................................. A61B 5/02
[52] U.S. Cl. ......................... 128/673; 128/748; 128/772
[58] Field of Search ............................... 128/657, 658, 128/672, 673, 675, 691, 692, 748, 772, 637; 607/119, 120, 122

[56] References Cited

U.S. PATENT DOCUMENTS

| | | | |
|---|---|---|---|
| 4,195,637 | 4/1980 | Grüntzig et al. | 128/348 |
| 4,712,566 | 12/1987 | Hök | 128/748 |
| 4,718,425 | 1/1988 | Tanaka et al. | 128/673 |
| 4,796,641 | 1/1989 | Mills et al. | 128/748 |
| 4,846,191 | 7/1989 | Brockway et al. | 128/748 |
| 4,850,358 | 7/1989 | Millar | 128/637 |
| 4,887,610 | 12/1989 | Mittal | 128/733 |
| 4,941,473 | 7/1990 | Tenerz et al. | 128/637 |
| 4,960,411 | 10/1990 | Buchbinder | 604/95 |
| 5,022,396 | 6/1991 | Watanabe | 128/642 |
| 5,025,786 | 6/1991 | Siegel | 128/642 |
| 5,046,497 | 9/1991 | Millar | 128/673 |
| 5,067,491 | 11/1991 | Taylor, II et al. | 128/673 |
| 5,085,223 | 2/1992 | Lars et al. | 128/675 |
| 5,113,868 | 5/1992 | Wise et al. | 128/673 |
| 5,131,406 | 7/1992 | Kaltenbach | 128/772 |
| 5,142,155 | 8/1992 | Mauze et al. | 250/458.1 |
| 5,280,786 | 1/1994 | Wlodarczyk et al. | 128/634 |
| 5,297,437 | 3/1994 | Schneider | 73/705 |
| 5,330,451 | 7/1994 | Gabbay | 604/284 |
| 5,395,353 | 3/1995 | Scribner | 604/264 |
| 5,437,637 | 8/1995 | Lieber et al. | 128/673 |

OTHER PUBLICATIONS

Borky et al., "Integrated Signal Conditioning for Silicon Pressure Sensors", IEEE Transactions on Electron Devices, vol. ED-26, No. 12, Dec. 1979.

Primary Examiner—Jennifer Bahr
Assistant Examiner—Bryan K. Yarnell
Attorney, Agent, or Firm—Townsend and Townsend and Crew LLP

[57] ABSTRACT

A guide catheter includes a tubular body having a proximal end and a distal end. A pressure or other sensor is disposed at or near the distal end of the body, preferably having an active surface thereof disposed away from the direction of blood flow when the catheter is present in a particular blood vessel, such as the aorta adjacent to a coronary ostium.

23 Claims, 3 Drawing Sheets

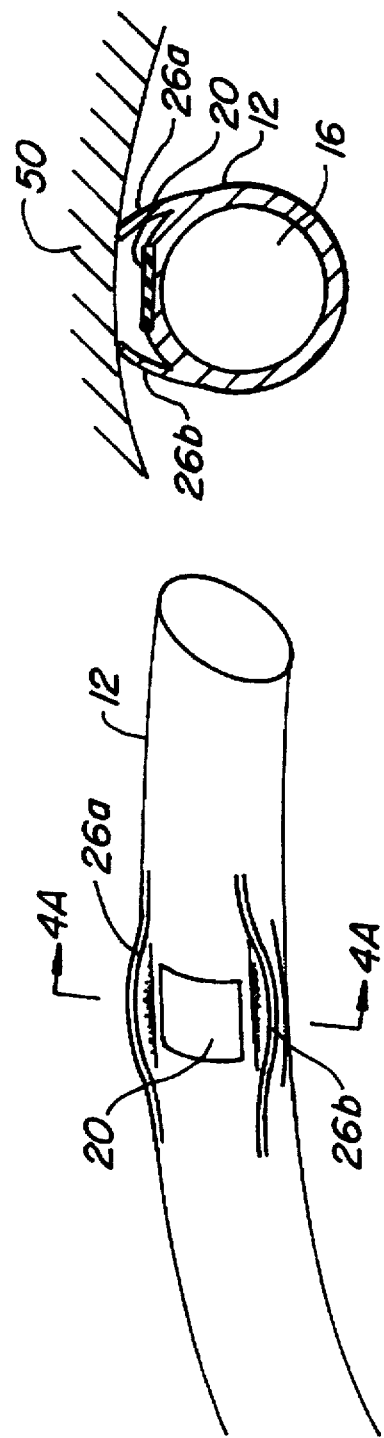

GUIDE CATHETER WITH SENSING ELEMENT

BACKGROUND OF THE INVENTION

1. Field of the Invention

The present invention relates to medical devices for providing access to the vascular system, and more particularly to a guide catheter for introducing an intravascular catheter to a coronary ostium.

2. Description of the Background Art

Many cardiac interventional procedures are known, for example angioplasty, atherectomy, angiography, and stent delivery, in which an interactive catheter is inserted into the vasculature of a patient, and maneuvered to a treatment site in the coronary vasculature surrounding the heart. The catheter is typically inserted into the femoral artery in the patient's groin area.

To position the interventional or interactive catheter at the desired treatment site, a guide catheter is first inserted through an introducer sheath and over a first guide wire into the artery, and maneuvered, through the vasculature to the desired engagement with one of the coronary ostia. Following the placement of a second guide wire through the guide catheter and into the coronary tree, the interactive catheter is then inserted over the guide wire and through the guide catheter and maneuvered to the desired location.

During such procedures, blood pressure is normally measured by a transducer located outside the body at a manifold attached to the proximal end of the guide catheter and fluidly connected to the annular gap between the interactive catheter shaft and the guide catheter lumen. The amplitude and quality of the pressure measurements are dependent upon blood pressure traveling along the fluid in the guide catheter and through any additional extension tubing or manifolds to reach the transducer. It is often desirable to use as small a guide catheter as possible, to minimize clinical complications associated with the arterial puncture in the groin. Eight French (2.66 mm) guides are standard, but seven French or six French guides are also commonly used, particularly for diagnostic procedures. The annular cross-sectional area between the internal wall of the guide catheter lumen and the exterior of the interactive catheter, which accommodates the fluid through which the blood pressure must be transmitted, can thus be severely restricted. This will result in damping of the blood-pressure signal, accompanied by a loss of accuracy and definition. In addition, it is not possible to maintain accurate measurements of blood pressure while a more viscous fluid, for example radiopaque contrast fluid, is being injected into the patient.

In U.S. Pat. No. 4,850,358, there is disclosed a catheter tip for insertion along a guide wire which may be inserted directly into a patient, or when used in connection with cardiac catheterization may be inserted through the lumen of a guide catheter, to directly measure the distal pressure in the blood vessel. This patent is assigned to Millar Instruments, Inc., who also manufacture such catheters with tip-mounted pressure sensors, and having an internal lumen for injection of radiopaque contrast media. While these catheter-mounted sensors may alleviate some of the problems associated with transducers mounted outside the body in diagnostic applications, they need to be positioned at the site at which blood pressure is to be measured, for example by insertion through a guide catheter. However, these devices are not capable of operation in conjunction with an interactive catheter (for example an angioplasty catheter, an atherectomy device or stent-placement device, or intravascular ultrasound catheter). Thus, these devices do not provide a solution to the problem of providing an accurate, undamped blood-pressure measurement simultaneously with use of a further interactive catheter.

U.S. Pat. No. 4,712,566 discloses a pressure sensor which can be inserted into a catheter for physiological pressure monitoring. U.S. Pat. No. 4,941,473 discloses a guide wire provided with a sensor at the distal end thereof. U.S. Pat. No. 5,280,786 discloses a fiber-optic based sensor for transcutaneous placement into a blood vessel. U.S. Pat. No. 5,142,155 discloses a further fiber-optic based pressure sensor. U.S. Pat. No. 5,085,223 discloses a miniaturized pressure sensor having means for protection of a diaphragm. U.S. Pat. No. 5,046,497 discloses a structure for coupling a guide wire and a catheter, to enable the guide wire to be inserted into a guide catheter, and multiple devices to be threaded along the guide wire. U.S. Pat. No. 5,025,786 discloses a device for detecting and diagnosing myocardial ischemia, which enables simultaneous measurement of pressure and electrical activity. U.S. Pat. No. 4,846,191 discloses an implant for chronic measurement of blood pressure. U.S. Pat. No. 4,796,641 also discloses an implant for chronic measurement of blood pressure. U.S. Pat. No. 4,195,637 discloses a dilation catheter incorporating a pressure sensor for monitoring dilation of a blood vessel. U.S. Pat. No. 4,960,411 discloses a steerable catheter, which in one embodiment is provided with pressure sensing at the distal end. U.S. Pat. No. 5,022,396 discloses a catheter capable of simultaneously measuring action potential of myocardial cells, and endocardiac cavity pressure. U.S. Pat. No. 4,718,425 discloses a catheter which has a pressure sensor for insertion into the left ventricle of an animal for continuous monitoring of blood pressure. U.S. Pat. Nos. 5,297,437 and 4,887,610 disclose devices for measuring pressure in the esophagus and in a human sphincter respectively. U.S. Pat. No. 5,395,353 discloses a guide catheter with controllable perfusion ports. U.S. Pat. No. 5,330,451 discloses a perfusion cannula.

None of these documents, the disclosure of each of which is herein incorporated by reference, discloses a guide catheter having a pressure sensing element, to enable accurate and undamped pressure measurement to be carried out while a further interventional catheter is located within the lumen of the guide catheter.

SUMMARY OF THE INVENTION

The present invention at least partially overcomes the above drawbacks by providing an apparatus and method with which blood pressure and other parameters can reliably and accurately be measured at the base of the aorta, while an interventional catheter is positioned within a guide catheter, to perform, for example, an angioplasty, atherectomy, drug delivery, stent placement or other procedure in the coronary arteries.

To accomplish the above and other objects, the present invention provides a guide catheter suitable for insertion into the vasculature of a patient, having an outer wall, and an inner luminal surface defined therein adapted for insertion of an interactive catheter, wherein at least one sensing element, usually a pressure sensing element but optionally a temperature or other sensing element, is provided in the wall, preferably adjacent a distal end of the guide catheter. In an exemplary embodiment, the pressure sensor is a silicon piezoresistive element. Preferably, the guide catheter is adapted for positioning of the sensor near or adjacent a coronary ostium, e.g., it will have a shaped distal end which conforms to the vasculature in the region of the ostia. Aortic blood pressure can be measured with a sensor so placed.

In a preferred embodiment, at least one spacing member, for example, comprising one or more flexible flaps is provided on the exterior wall of the catheter to maintain the sensor spaced away from the wall of a blood vessel (e.g., aorta) in which the catheter is located. In addition, or alternatively, the catheter may be shaped or geometrically configured to maintain the sensor spaced from a blood-vessel wall.

In another preferred embodiment, the sensor is mounted on a resiliently biased portion of the exterior wall of a catheter. In this way, the sensor may be deformed inward, for example, upon insertion through an introducer sheath, so that even if the sensor increases the overall diameter of the guide catheter, the size of the hole required for insertion is not significantly increased. The resilient biasing may be provided, for example, simply by mounting the sensor in the wall of the catheter, and providing one or more slits in the wall of the catheter adjacent the sensor, to enable a portion of the catheter wall to be temporarily deformed inwardly, until it reaches the distal end of the introducer sheath and exits therethrough.

In a preferred construction, the sensor is integrated with the wall of the guide catheter, for example, by heat bonding. Wires for transmitting signals from the sensor to the exterior of the patient may be embedded in the wall of the guide catheter. The sensor will preferably be disposed so that its major surface is facing radially outward, with the minor dimension in or adjacent to the wall in order to reduce the profile of the catheter.

The present invention provides a method for obtaining measurements from the interior of the vascular system of a patient, comprising providing a guide catheter having an exterior wall defining an inner lumen for insertion of an interactive catheter, and having at least one pressure or other sensing element mounted in the exterior wall; inserting the guide catheter into the vasculature of a patient, and maneuvering the catheter to a desired location; and obtaining measurements from said sensor.

In preferred embodiments, the method further comprises introducing an interactive catheter through said lumen, and measuring with said sensor while said interactive catheter is within the lumen.

BRIEF DESCRIPTION OF THE DRAWINGS

FIG. 3 shows an exemplary comparison between pressure measurements with a conventional external transducer, and measurements taken with a transducer mounted at the base of the aorta;

FIG. 4 is a schematic perspective view of a modified embodiment of the present invention;

FIG. 4A is a section taken at A—A in FIG. 4;

DESCRIPTION OF THE PREFERRED EMBODIMENTS

Figure 1:
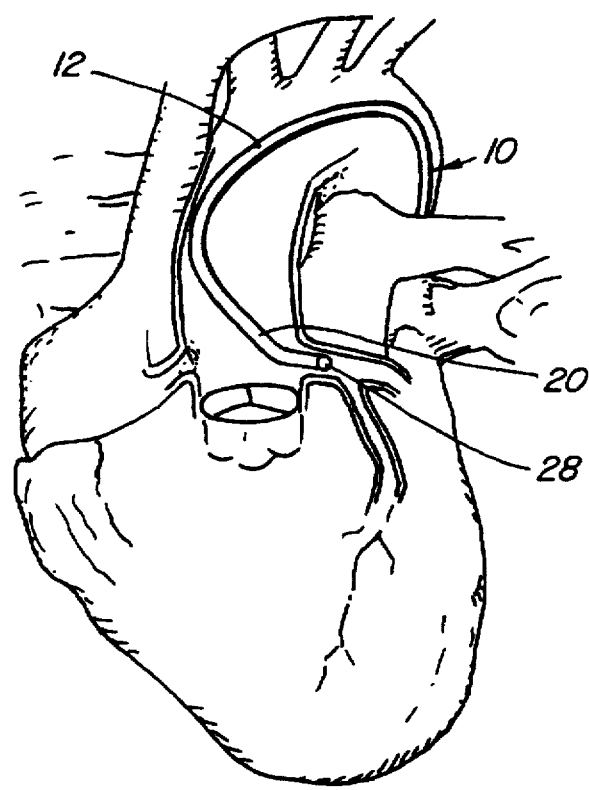
FIG. 1 is a schematic perspective view of a catheter according to the invention located at a coronary ostium.
Figure 2:
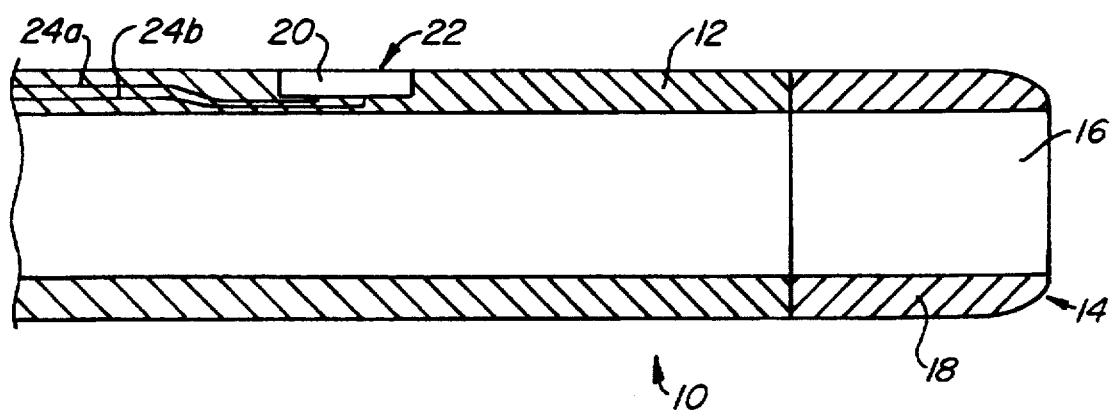
FIG. 2 is a schematic cross-section of a catheter according to the invention.

Referring to FIGS. 1 and 2, a preferred embodiment of a guide catheter with a built-in transducer comprises a tubular body 12 having a distal end 14 and a proximal end (not shown). The tubular body 12 is approximately 1 meter long, although this length may vary depending on the application. The profile is chosen appropriately for the interactive catheters to be used, typical sizes being 6 French, 7 French, or 8 French. The material of the tubular-body 12 has a degree of flexibility, and may incorporate a braid of thin stainless steel wire or carbon fiber to increase its axial stiffness, pushability and resistance to kinking. As can be seen in FIG. 2, the tube has an internal lumen 16, which is open at both ends, and sized to accommodate an interactive catheter. The internal wall may be lined with PTFE or other lubricious material, to reduce friction between the interactive catheter and the tube wall. A short portion of softer, low durometer, material smoothly curved into an atraumatic tip 18 is attached, for example, by heat bonding. The proximal end of the tube (not shown) terminates in a standard ISO Luer fitting, to which a valve or manifold may be attached. The distal portion of the catheter is shaped to move around the aortic arch 10, engage the desired coronary ostium as shown in FIG. 1 at 28 and provide support against the aortic wall when an interactive catheter (not shown) is traversed through its lumen. Such interventional devices and methods are well-known in the art. Similar constructions of guide catheters are well known in the art, and any of a number of these may form the basis for manufacturing a catheter according to the invention. As described thus far, the construction of the guide catheter is entirely conventional, and it is intended that the provision of pressure sensor may be accomplished by modifying otherwise conventional designs as described in more detail below.

The catheter of the invention differs from prior art catheters in that a sensing element 20, for example a piezoresistive silicon pressure transducer, e.g., one available from Lucas NovaSensor in Fremont, Calif., is embedded in the exterior wall of the tubular body 12. For the sensing element, other sensors may be used, e.g., a strain gauge. In this embodiment, employing a piezoresistive sensor, the pressure sensing face 22 of the sensor 20 is directly exposed on the exterior of the tubular body 12. In some applications, it may be desirable to embed the sensing element 20 more deeply in the wall of the tubular body 12, or to provide a covering over the surface of the sensor, provided the sensor is still able to function with the required accuracy and lack of damping; in some circumstances it may even be desirable to have the sensor exposed on the inner wall of the tubular body 10. It can be seen that the sensor is positioned relatively close to the distal end 14 of the tubular body 12, typically within 5 cm, so the measured pressure will be the true "static" pressure of blood from the left ventricle of the heart during the cardiac cycle. This implies the surface 22 of pressure sensor 20, should preferably face away from the aortic valve exit.

While the sensing element 20 will usually be a pressure sensor intended for the direct measurement of pressure at or near a coronary ostium, it may also be a pressure or temperature sensor configured to measure another parameter, such as blood flow velocity or temperature. For example, the sensor could be a heated thermistor configured to measure blood flow velocity. Alternatively, a pair of pressure sensors could be arranged as a Pitot-static velocity gauge. Another alternative would be to provide a thermocouple or other temperature transducer for direct temperature measurement.

When the sensor is exposed at the exterior of the guide catheter, it is preferable to ensure that the sensor will not come into direct contact with an artery wall, as this may lead to inaccurate readings.

One way of achieving this while having pressure sensor surface 22 also face away from the aortic valve is shown in FIG. 1; the sensor 20 is located at a position on the guide catheter 10 in relation to the curvature of the catheter at which arterial contact is highly unlikely. This will be achievable for the majority of conventional left and right guide catheter shapes. As can be seen in the exemplary case of FIG. 1, a portion of the distal end of the guide catheter protrudes into the ostium of the left coronary artery, and another portion curves around the aortic arch, the sensor being located between these portions, so that it is maintained substantially away from any of the walls of the aorta. In the prior art, guide catheters have been provided with side holes for improved perfusion of the coronary vasculature during interventional procedures, the position of which has also been selected to avoid tissue contact. The sensor of the invention could be placed at a similar location. Other arrangements, for example, using spacers or protective covering may be used. An example of a spacer will be described below with reference to FIG. 4.

Signal leads 24a, 24b carry electrical signals to and from the transducer 20 to circuitry located outside the body. In the embodiment shown, there are only two leads, but the sensing element may include a bridge arrangement, or other circuitry, for example signal-processing circuitry, or temperature compensation elements, in which case more leads will usually be required. The sensing element 20 is typically heat-bonded into place in the wall of the guide catheter, and this may be achieved with the assistance of a mold, for maintaining the profile of the catheter, as well as for preventing molten polymeric material flowing into undesired places. The wires 24a, 24b for transmission of the signal may be embedded within the catheter wall, for example by heat-bonding the wires into a pre-formed catheter tube, or by extruding the catheter shaft with the wires in place. Alternatively, the wires may be retained on the exterior of the catheter, for example by thin heat-shrinkable tubing.

Referring to FIG. 3, an exemplary comparison between the pressure at the exterior face 22 of the sensor 20 (aortic pressure transduction) and the pressure measurement obtained using a conventional arrangement, at the proximal end of a catheter is shown. As can be seen in this representation, although the cardiac pressure signal may still be discernable with a conventional pressure sensor arrangement, as the bore of the guide catheter is restricted, the damping is increased and the accuracy of the measurement is reduced.

Another method of maintaining the sensor away from the artery walls is depicted in FIG. 4. In this embodiment, a spacing arrangement, comprising two flaps 26a, 26b, located on either side of the sensor 20, ensures that even if contact with the artery walls were to occur, the flaps would contact the artery wall first, allowing the sensor 20 to be directly exposed to blood. This can best be understood with reference to the section shown in FIG. 4A which shows the flaps in contact with an artery wall 50. The flaps, preferably made from a suitable polymeric material, should be flexible, for ease of insertion of the catheter, and to minimize the risk of damage to the arteries, but should be sufficiently stiff to resist collapsing completely, as this would impair the operation of the sensor.

Figure 5A:
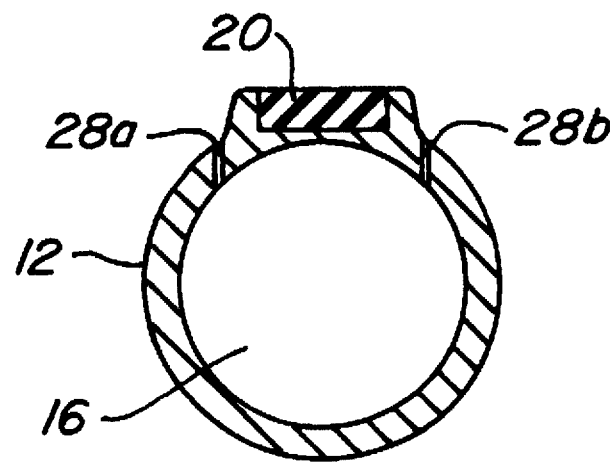
FIG. 5A is a section through a further embodiment of the present invention.
Figure 5B:
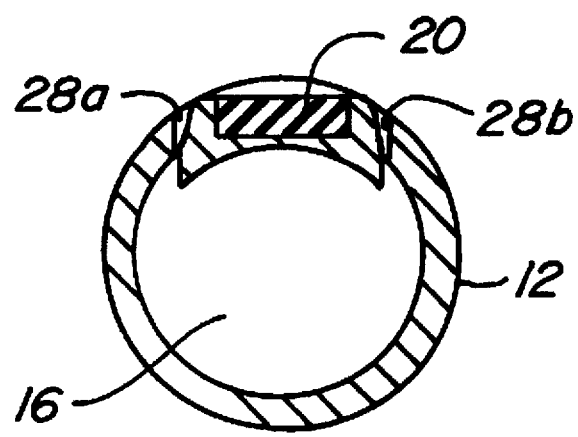
FIG. 5B shows the section of FIG. 5A in an inwardly deformed state for introduction through an introducer sheath.

In the schematic view shown in FIG. 2, the sensor element is embedded entirely within the wall of the catheter. However, there may be instances where the sensor 20 is thicker than the wall of the tubular element 12, or does not match the curvature of the tubular element 12 which may lead to a bulge in the guide catheter at the location of the sensor. This in turn, may cause difficulties in introducing the guide catheter 10 through the introducer sheath, or may require the use of a larger introducer sheath. One way of overcoming such difficulty is shown in FIGS. 5A and 5B.

As can be seen, the profile of the tube 12 bulges outwardly at the location of the sensing element 20. Parallel slits 28a, 28b either side of the sensing element 20, and parallel to the longitudinal axis of the tubular body 12, allow the portion of the tubular body 12 on which the sensing element 20 is mounted to stretch slightly and to deform inwardly, to a configuration shown in the section in FIG. 5B. The precise length and spacing of the slits will depend on the flexibility of the material of the tube wall, but typically these slits may be one or two centimeters long. If the material is more rigid, the slits may be longer, or a transverse cut may also be made (preferably on the distal side so that the wires can run directly to the proximal end of the tube wall), to form a U-shaped cut around the sensor, so that the sensor is mounted on a tongue of material that is free to deform inwardly. In cutting out the tongue, care must be taken to ensure that any reinforcement or braid incorporated in the wall of the guide catheter does not leave protruding strands or sharp edges.

Referring back to FIG. 1, the method of operation of the catheter will now be described. As can be seen in the figure, a catheter 10 according to the invention having been inserted into an introducer sheath in the known manner, is positioned with its distal end engaged in a coronary ostium. With a catheter in this position, the pressure can be measured accurately and without damping by means of the sensing element 20, and this measurement may continue while interactive catheters, for example angioplasty catheters, or atherectomy devices, or stent-placement devices are inserted through the lumen of the guide catheter. Pressure measurement is minimally and only temporarily affected by injection of a contrast fluid through the guide catheter, so it is generally possible to perform continuous, accurate monitoring of blood pressure throughout any interventional procedure.

The above describes preferred embodiments and methods, but it will be understood by those skilled in the art that many variations and modifications can be made without departing from the spirit of the invention. For example, other sensing elements may be used, and measurement of parameters other than blood pressure may be provided.

What is claimed is:

1. In a guide catheter having a distal end suitable for insertion into a vessel in the vasculature of a patient and a proximal end which remains outside the patient, wherein the distal end has a predetermined shape accessing a coronary ostium, the catheter having an outer wall and a lumen defined therein, said lumen being adapted for insertion of an interactive catheter and having an open distal end, the improvement comprising at least one pressure sensing element provided in the outer wall of the guide catheter, wherein an active surface of the sensing element faces away from the direction flow of blood when the catheter is positioned adjacent the coronary ostium.

2. A guide catheter according to claim 1, wherein the sensing element is a piezoresistive pressure transducer, adapted for measuring blood-pressure of the patient.

3. A guide catheter according to claim 1, wherein the sensing element is located within 5 cm of the distal end of the catheter.

4. A guide catheter according to claim 1, wherein the distal end of said guide catheter has a predetermined shape for insertion into said vessel to maintain at least one portion of said distal end spaced from a wall of said vessel, and wherein the sensing element is mounted on said at least one portion.

5. A guide catheter according to claim 1, comprising at least one spacing member on the outer wall of the catheter, for maintaining the sensing element spaced from a wall of a blood vessel of the patient.

6. A guide catheter according to claim 1, wherein the sensing element is mounted on a resiliently biased portion of the wall of the catheter, so that the sensing element may be displaced inwardly with respect to the wall of the catheter.

7. A guide catheter according to claim 1, wherein the sensing element is integrated with the wall of the guide catheter.

8. A guide catheter according to claim 1, wherein said outer wall is provided with signal leads for carrying signals from said sensing element to the exterior of the patient.

9. A method of obtaining pressure measurements from the interior of a vessel in the vascular system of a patient, said method comprising:

inserting into a vessel of the vascular system a guide catheter having an outer wall defining an internal lumen and having an open distal end for insertion of an interactive catheter and having at least one pressure sensing element mounted in the outer wall;

maneuvering the guide catheter to a desired location in an aorta of the patient so that the pressure sensing element is faced away from the direction of blood flow through the aorta; and obtaining measurements of the aortic blood from said sensing element.

10. A method according to claim 9, further comprising introducing an interactive catheter through said lumen, and measuring with said sensing element while said interactive catheter is within the lumen.

11. In a guide catheter having a distal end suitable for insertion into a vessel in the vasculature of a patient and a proximal end which remains outside the patient, wherein the distal end has a predetermined shape for accessing a coronary ostium, the catheter having an outer wall and a lumen defined therein, said lumen being adapted for insertion of an interactive catheter and having an open distal end, the improvement comprising at least one pressure sensing element provided in the outer wall of the guide catheter, wherein an active surface of the pressure sensing element faces away from the direction flow of blood when the catheter is positioned adjacent the coronary ostium and wherein at least one spacing member on the outer wall of the catheter maintains the pressure sensing element spaced from a wall of a blood vessel of the patient.

12. A guide catheter according to claim 11, wherein the sensing element is a piezoresistive pressure transducer, adapted for measuring blood-pressure of the patient.

13. A guide catheter according to claim 11, wherein the sensing element is located within 5 cm of the distal end of the catheter.

14. A guide catheter according to claim 11, wherein the pressure sensing element is mounted on a resiliently biased portion of the wall of the catheter.

15. In a guide catheter having a distal end suitable for insertion into a vessel in the vasculature of a patient and a proximal end which remains outside the patient, wherein the distal end has a predetermined shape for accessing a coronary ostium, the catheter having an outer wall and a lumen defined therein, said lumen being adapted for insertion of an interactive catheter and having an open distal end, the improvement comprising at least one pressure sensing element provided in the outer wall of the guide catheter wherein the sensing element is mounted on a resiliently biased portion of the wall of the catheter, so that the sensing element may be displaced inwardly with respect to the wall of the catheter.

16. A guide catheter according to claim 15, wherein the sensing element is a piezoresistive pressure transducer, adapted for measuring blood-pressure of the patient.

17. A guide catheter according to claim 15, wherein the sensing element is located within 5 cm of the distal end of the catheter.

18. A guide catheter according to claim 15, wherein the predetermined shape maintains at least one portion of said distal end spaced from a wall of said vessel, and wherein the pressure sensing element is mounted on said at least one portion.

19. In a guide catheter having a distal end suitable for insertion into a vessel in the vasculature of a patient and a proximal end adapted to remain outside the patient, wherein the distal end has a predetermined shape for accessing a coronary, ostium via the aortic arch including a distal end which is adapted to engage the coronary ostium, a curved portion which is adapted to traverse the aortic arch, and an intermediate portion between the curved portion and the distal tip, the catheter having an outer wall and a lumen defined therein, said lumen being adapted for insertion of an interactive catheter and having an open distal end, the improvement comprising at least one pressure sensing element provided in the outer wall of the guide catheter, wherein the pressure sensing element is disposed on the intermediate portion of said guide catheter so as to be maintained substantially away from the aortic wall.

20. A guide catheter according to claim 19, wherein the sensing element is a piezoresistive pressure transducer, adapted for measuring blood-pressure of the patient.

21. A guide catheter according to claim 19, wherein the sensing element is located within 5 cm of the distal end of the catheter.

22. A guide catheter according to claim 19, wherein the sensing element is mounted on a resiliently biased portion of the wall of the catheter, so that the sensing element may be displaced inwardly with respect to the wall of the catheter.

23. A guide catheter according to claim 19, further comprising at least one spacing member on the outer wall of the catheter, for maintaining the sensing element spaced from a wall of a blood vessel of the patient.

* * * * *